United States Patent
Sherry

(10) Patent No.: US 6,540,717 B2
(45) Date of Patent: Apr. 1, 2003

(54) IMPLANTABLE VASCULAR ACCESS DEVICE

(75) Inventor: John Sherry, Needham, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/957,619

(22) Filed: Sep. 20, 2001

(65) Prior Publication Data

US 2002/0013557 A1 Jan. 31, 2002

Related U.S. Application Data

(63) Continuation of application No. 09/398,887, filed on Sep. 20, 1999.

(51) Int. Cl.[7] ............................................. A61M 11/00
(52) U.S. Cl. .................................................. 604/93.01
(58) Field of Search ........................... 604/93.01, 8–10, 604/86–88, 173–175, 244

(56) References Cited

U.S. PATENT DOCUMENTS

| | | |
|---|---|---|
| 4,559,033 A | 12/1985 | Stephen et al. |
| 4,822,341 A | 4/1989 | Colone |
| 5,318,545 A | 6/1994 | Tucker |
| 5,562,617 A | 10/1996 | Finch, Jr. et al. |
| 5,713,859 A | 2/1998 | Finch, Jr. et al. |
| 5,755,780 A | 5/1998 | Finch, Jr. et al. |
| 5,792,123 A * | 8/1998 | Ensminger .................. 604/272 |
| 5,807,356 A | 9/1998 | Finch, Jr. et al. |
| 5,931,801 A * | 8/1999 | Burbank et al. ............... 604/4 |

* cited by examiner

Primary Examiner—Anhtuan T. Nguyen
Assistant Examiner—Ann Y Lam
(74) Attorney, Agent, or Firm—Hoffmann & Baron, LLP

(57) ABSTRACT

An implantable vascular access device includes a housing having an inlet, an outlet, an interior chamber defined therein and a valve positioned between the inlet and the interior chamber. The valve is subcutaneously manipulated between an open position, in which fluid can flow between the inlet and the interior chamber, and a closed position in which the valve occludes the inlet. The device may include any combination of multiple inlets, outlets and/or interior chambers. In the preferred embodiment, the housing includes two separate interior chambers suitable for the inflow and outflow of a typical hemodialysis procedure. A method for accessing a vascular structure is provided which includes the steps of subcutaneously implanting the device connecting one end of a cannula to the outlet of the device and another end of the cannula to a selected vascular structure. The valve of the device is manipulated to permit fluid communication between the inlet of the device and the selected vascular structure. A needle is introduced through the inlet opening to access the selected vascular structure.

18 Claims, 3 Drawing Sheets

IMPLANTABLE VASCULAR ACCESS DEVICE

This application is a continuation of copending application Ser. No. 09/398,887, filed on Sep. 20, 1999.

BACKGROUND OF THE INVENTION

1. Field of the Invention

The present invention relates to implantable vascular access devices used in the delivery and/or withdrawal of fluids to and from the body and more particularly relates to a self-sealing device which permits intermittent vascular access.

2. Description of the Prior Art

Conventional vascular access devices are surgically implanted under the skin to allow for intermittent access to a selected vascular structure, such as an artery or a vein, for introducing and/or withdrawing fluids to and from the selected vascular structure. Typically, such devices generally include an interior chamber having an outlet opening connected via a cannula to a vascular structure within the body and a penetrable membrane which serves as a cover for the interior chamber of the device. The penetrable membrane or septum is comprised of a material, such as silicone rubber, which automatically reseals itself after being penetrated by a hypodermic needle or a needle introduced catheter.

In operation, a needle passes through the skin and through the penetrable membrane into the interior chamber allowing fluid to be injected into the chamber and expelled through the cannula into the selected vascular structure or, conversely, fluid may be withdrawn. The advantages of an implantable device over acute catheter procedures include reduced infection, easier patient maintenance and improved aesthetics. Typical implantable vascular access devices are shown in U.S. Pat. No. 5,318,545 to Tucker and U.S. Pat. No. 5,755,780 to Finch, Jr. et al.

The advancement of modem hemodialysis procedures have brought with it the development of vascular access devices for the purpose of acquiring and returning large quantities of blood for passage through a hemodialysis unit. To facilitate adequate dialysis flow rates, relatively large diameter needles and/or catheters in the range of 14 gauge or higher are required. A major drawback of conventional vascular access devices, particularly those used in hemodialysis procedures, is the deterioration of the rubber membranes as a result of repeated penetration with such large gauge needles. Additionally, typical vascular access devices provide for only one needle port resulting in chronic breach of the skin at the same location. This in turn results in increased skin trauma and possible infection.

Accordingly, it is desirable to provide a vascular access device which can withstand multiple insertions with a large diameter needle and which provides reduced skin trauma and easier patient maintenance.

OBJECTS AND SUMMARY OF THE INVENTION

It is an object of the present invention to provide a vascular access device which can withstand a high number of large gauge needle insertions without deterioration.

It is another object of the present invention to provide a vascular access device which is easily subcutaneously manipulated and which prevents the escape of fluids from the device.

It is yet another object of the present invention to provide a vascular access device having multiple needle ports thereby reducing the skin trauma caused by repeated needle sticks at the same location.

It is still a further object of the present invention to provide a vascular access device suitable for hemodialysis procedures which incorporates two interior chambers into a single body.

In accordance with one form of the present invention, a vascular access device generally includes a housing having an inlet, an outlet, an interior chamber defined therein and a valve positioned between the inlet and the interior chamber. The valve is movable between an open position, in which fluid can flow between the inlet and the interior chamber, and a closed position in which the valve occludes the inlet. Preferably the valve comprises an elongate member having a through-hole formed therein which aligns with the inlet when the valve is in the open position. One or both ends of the elongate member protrudes through the housing and is palpable through the skin of the patient. The elongate member is resiliently urged to its closed position by a spring and is opened by subcutaneously pressing the end of the member protruding through the housing.

The present invention may include any combination of multiple inlets, outlets and/or interior chambers. In the preferred embodiment, the housing includes two separate interior chambers suitable for the inflow and outflow of a typical hemodialysis procedure. The device further includes multiple inlets in fluid communication with each interior chamber. Several elongate members are moved simultaneously to an open position by a single push button protruding through the outer surface of the housing. Each elongate member includes throughholes which are aligned with respective inlets when the push button is depressed to move the elongate members to their open position. When the button is released, a spring urges the elongate members to their closed position thereby occluding the inlets. Each interior chamber is in fluid communication with an outlet which is connected to a selected vascular structure by means of a cannula for permitting fluid communication between the vascular structure and the interior chamber of the device.

A method for accessing a vascular structure is provided which includes the steps of surgically implanting a device as described above, connecting one end of a cannula to the outlet of the device and another end of the cannula to a selected vascular structure, subcutaneously manipulating the valve of the device for permitting fluid communication between the inlet of the device and the selected vascular structure and introducing a needle or a needle-introduced catheter through the inlet opening to access the selected vascular structure.

A preferred form of the vascular access device, as well as other embodiments, objects, features and advantages of this invention will be apparent from the following detailed description of illustrative embodiments thereof which is to be read in conjunction with the accompanying drawings.

DETAILED DESCRIPTION OF THE PREFERRED EMBODIMENTS

Figure 1A:
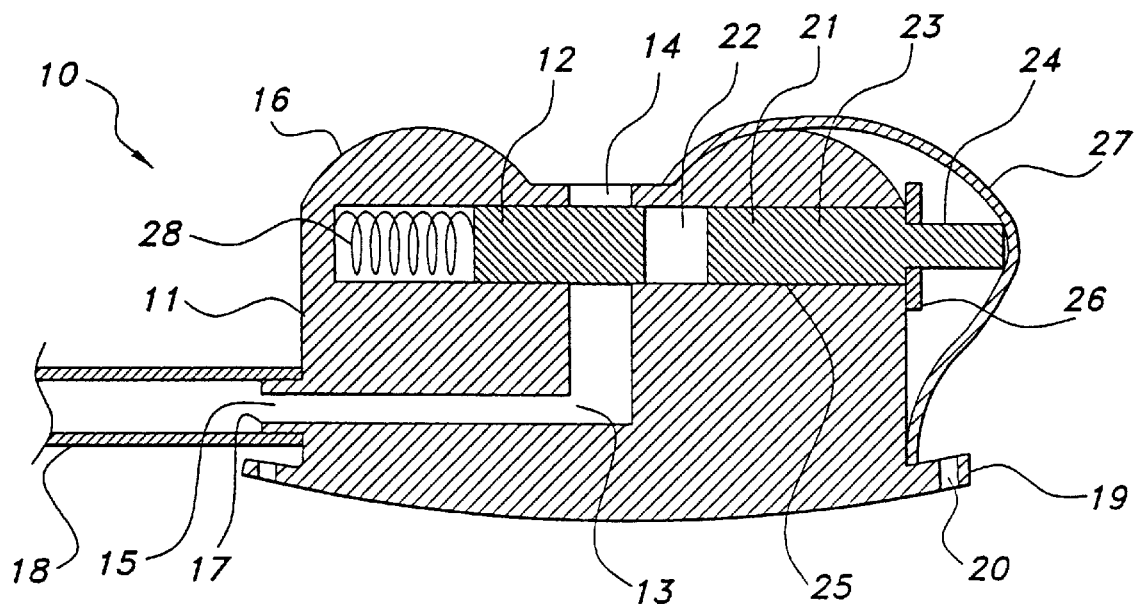
FIGS. 1A and 1B are cross-sectional views of the vascular access device formed in accordance with the present invention showing the valve in its closed and open positions, respectively.
Figure 1B:
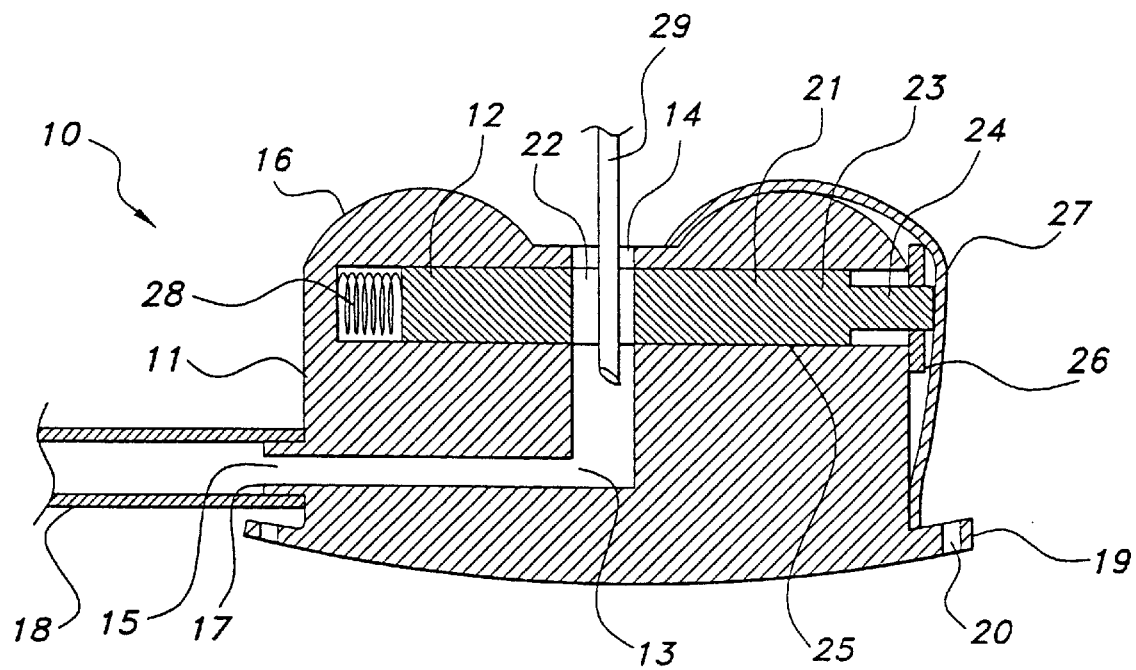

Referring to FIGS. 1A and 1B, an implantable vascular access device formed in accordance with the present invention is shown. The vascular access device 10 is designed to be surgically implanted under the skin and generally includes a housing 11 and a valve 12. The housing 11 and the valve 12 may be made from any suitable biocompatible material possessing sufficient hardness to resist being damaged or gouged by needles or other devices which will be repeatedly inserted into the device. Plastic constructions are advantageous in that they are inexpensive to fabricate utilizing conventional molding techniques and are available in a variety of biocompatible materials. Surgical metals, however, are also suitable.

The housing 11 includes an interior chamber 13 formed therein, and an inlet 14 and an outlet 15 extending through an external surface 16 of the housing and communicating with the interior chamber. The outlet 15 may be formed with a cuff 17 to facilitate connection to a cannula 18. The opposite end (not shown) of the cannula is connected or grafted to a selected vascular structure (e.g. an artery or a vein) in a conventional manner. The housing 11 also includes a peripheral rim 19 having apertures 20 for securing the device to fascia underlying the skin by means of sutures threaded through the peripheral apertures.

The valve 12 preferably comprises an elongate member 21 having a transverse bore or through-hole 22 formed in a body portion 23 thereof. The elongate member 21 further includes a neck portion 24 for accommodating a spring 25. To maintain the proper orientation of the elongate member 21 with respect to the inlet openings 14, the neck portion 24 and/or the body portion 23 is formed with a non-circular cross-section which prevents the elongate member from rotating when fitted in close sliding relationship within a correspondingly sized support hole 26 or 27 formed in the external surface 16 of the housing 11. The opposite ends of the elongate member 21 are slidably supported by and protrude through the support holes 26 and 27 of the housing 11. Sealing rings (not shown) may be provided on the elongate member 21 to prevent leakage from the support holes 26 and 27. The spring 25 is also made from a biocompatible material and is captured around the neck portion 24 between the internal surface of the interior chamber 13 and the body portion 23 for resiliently urging the elongate member 21 to its closed position, i.e., to the right as shown in FIGS. 1A and 1B. A retaining clip 28 is fixed to the protruding end of the neck portion 24 to retain the elongate member 21 in its closed position within the housing 11. Although a spring is preferred, other biasing devices, such as internally molded magnets, may also be utilized for resiliently urging the elongate member 21 to its closed position.

In use, the vascular access device 10 is surgically implanted such that it is entirely subcutaneous. In its normally closed position, the body portion 23 of the elongate member 21 blocks or occludes the inlet opening 14 thereby preventing fluid communication between the inlet and the interior chamber 13. When the protruding end of the body portion 23 is subcutaneously depressed, the elongate member 21 moves to its open position in which the transverse throughhole 22 aligns with the inlet opening 14 thereby permitting fluid communication between the inlet opening and the interior chamber 13 through the elongate member. When the valve 12 is in its open position, a needle 29 or a needle-introduced catheter may be percutaneously inserted through the inlet 14 into the interior chamber 13 to introduce or withdraw fluid from the selected vascular structure via the cannula 18. Once the needle 29 is inserted, the needle will hold the elongate member 21 in its open position thereby allowing the protruding end of the body portion 23 to be released. Once the needle 29 is removed, the spring 25 will automatically return the elongate member 21 to its closed position in which the inlet opening 14 is again occluded and blood reflux is prevented.

Figure 2A:
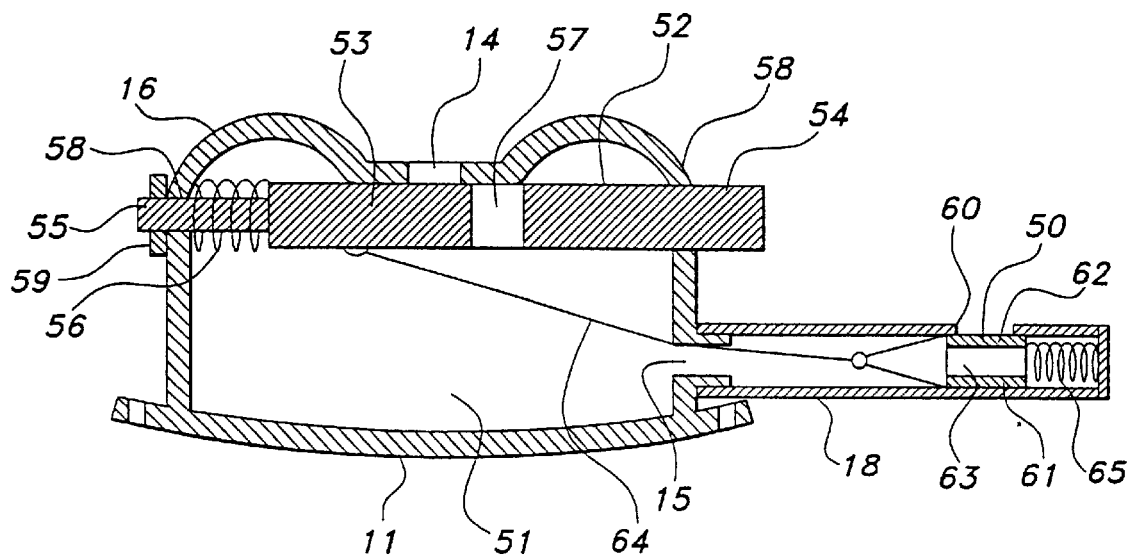
FIG. 2 a perspective view of the preferred embodiment of the device shown in FIG. 1.
Figure 2B:
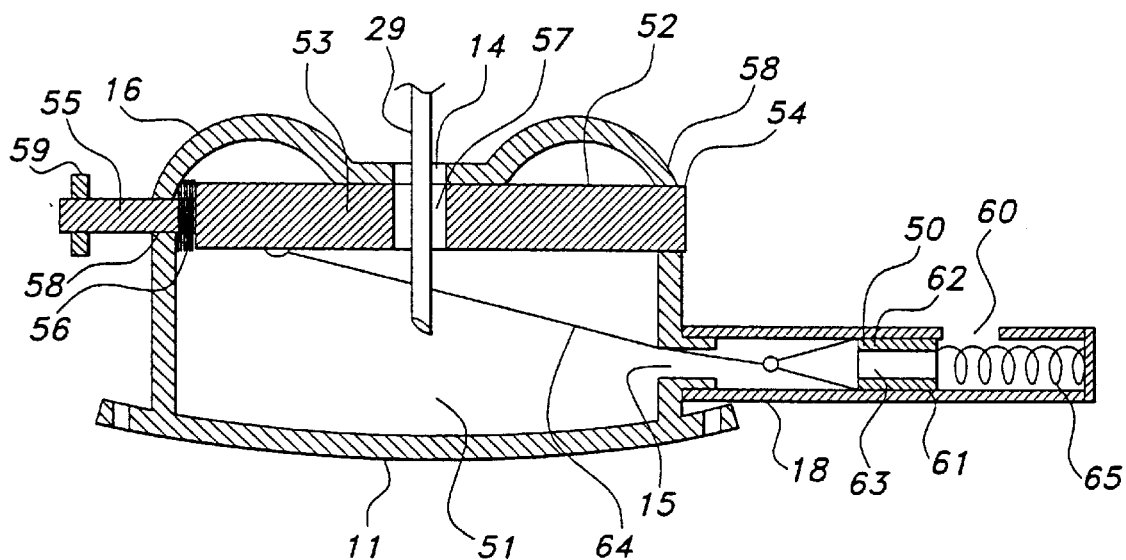
Figure 3:
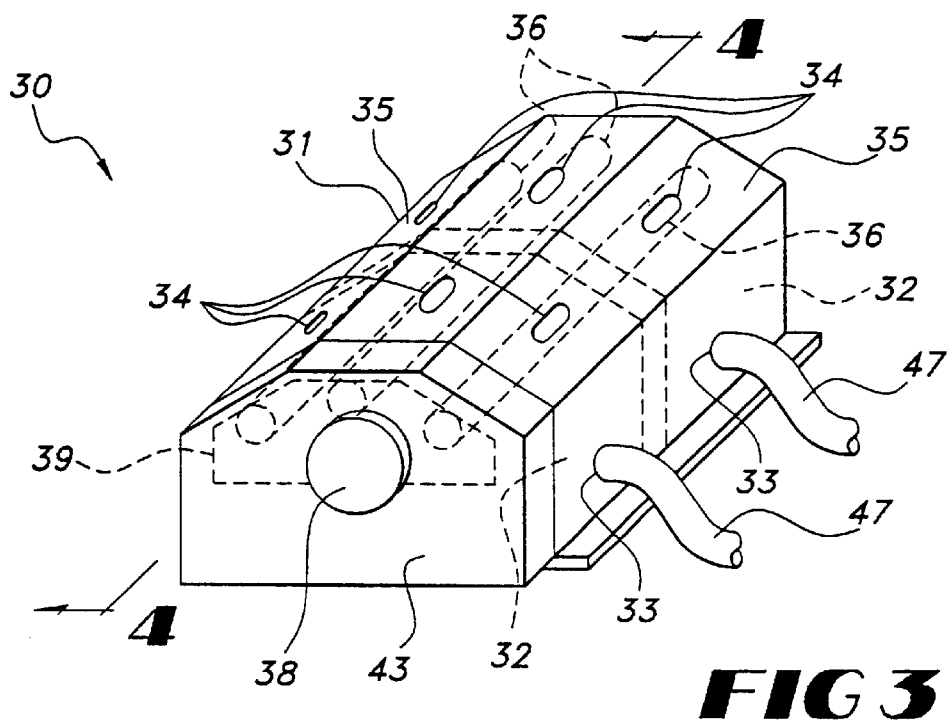
FIG. 3 is a cross-sectional view of the device shown in FIG. 2 taken along the line 3—3.
Figure 4:
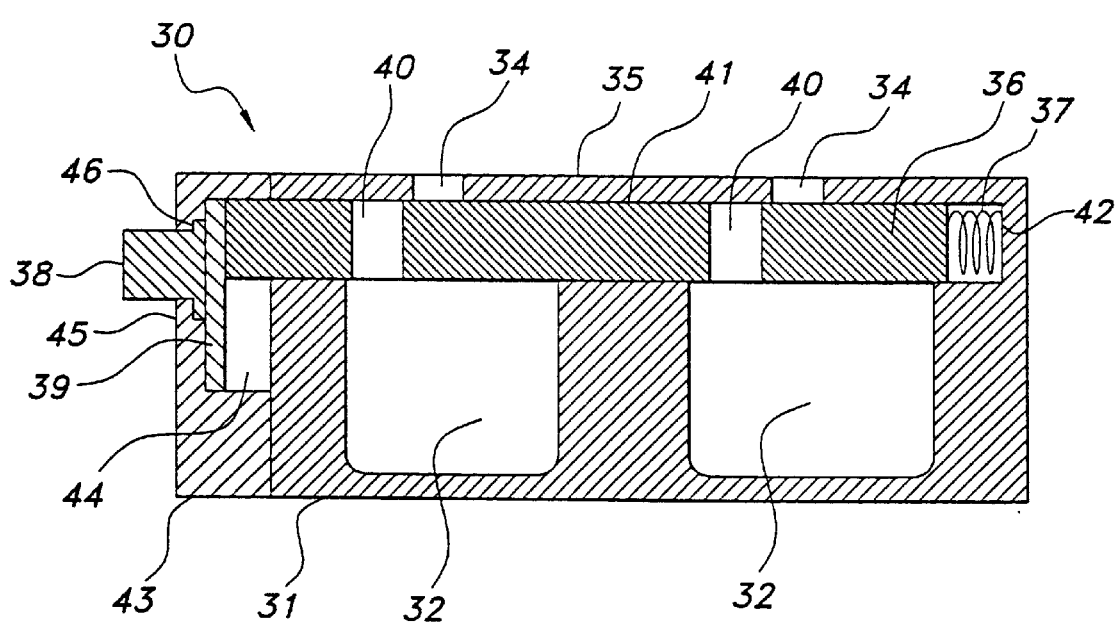
FIG. 4 is a cross-sectional view of the device shown in FIG. 3 taken along line 4—4.

Referring now to FIGS. 2 and 3, a preferred form of the implantable vascular access device 30 is shown. The multi-port device 30 shown in FIGS. 2 and 3 includes a housing 31 formed with two separate interior chambers 32, an outlet 33 in fluid communication with each interior chamber and a plurality of inlets 34. The housing 31 shown in FIGS. 2 and 3 includes three external access surfaces 35 each with a pair of inlets 34 which communicate with a respective interior chamber 32. However, any geometric configuration for the housing, such as additional access surfaces, additional interior chambers or additional inlets may be utilized.

The multi-port device 30 includes a valve which comprises three elongate members 36 each having a spring 37 fixed at one end thereof and a push button 38 with a push plate 39 adjacent the other end. The elongate members 36 are formed with transverse through-holes 40, as described above, and are slidably supported in longitudinal bores 41 formed in the housing. The springs 37 are captured between the elongate members 36 and the bottom walls 42 of the longitudinal bores 41 formed at one end of the housing 31. An end cap 43 is fixed to the opposite end of the housing 31 for retaining the push button 38 and the push plate 39. The end cap 43 is formed with a recess 44 for retaining the push plate 39 and a counter bored opening 45 through which the push button 38 protrudes. The push button 38 is formed with a shoulder portion 46 which is retained by the counter bored opening 45 so that the push button is held within the end cap 43. The depth of the recess 44 allows the push plate 39 to travel a predetermined distance when the push button 38 is depressed.

Operation of the multi-port device 30 is similar to that as described above. The springs 37 resiliently urge each of the individual elongate members 36 into their normally closed position in which the elongate members occlude the inlet openings 34. When the push button 38 is subcutaneously depressed, the elongate members 36 are simultaneously moved to their open position by the push plate 39 (i.e., to the right as shown in FIG. 3) wherein the transverse through-holes 40 of the elongate members align with respective inlet openings 34. Again, the elongate members 36 may be formed with non-circular cross-sections so that their proper orientation with respect to the inlets 34 is maintained. Once the elongate members 36 are moved to their open position any one or more of the inlets 34 may be accessed with a needle for withdrawing or introducing fluid through the interior chambers 32. In a typical hemodialysis procedure, an infusion needle is inserted through an inlet 34 into one of the interior chambers 32 and an aspiration needle is inserted through another inlet into the other separate chamber. The interior chambers are in fluid communication with at least one selected vascular structure by means of the cannulas 47, as described above. Again, once the needles are inserted the push button 38 may be released and upon removing the needle the springs 37 automatically urge the elongate members 36 back to their normally closed position. Preferably, needles should be inserted in corresponding pairs of inlets 34 on the same access surface 35 so that when the push button 38 is released the remaining elongate members not being accessed will return to their closed position.

As a result of the present invention, a multi-port vascular access device is provided which can withstand numerous needle insertions without deterioration. Additionally, the multi-port design allows for needle insertion at different locations on the skin thereby allowing the skin more time to heal before reinsertion of a needle. Furthermore, the dual interior chamber design of the present invention is particularly suitable for hemodialysis procedures requiring simultaneous inflow and outflow.

Although the illustrative embodiments of the present invention have been described herein with reference to the accompanying drawings, it is to be understood that the invention is not limited to those precise embodiments, and that various other changes and/or modifications may be effected therein by one skilled in the art without departing from the scope or spirit of the invention, and it is intended to claim all such changes and/or modifications as fall within the scope of the invention.

What is claimed is:

1. A surgically implantable device for permitting intermittent vascular access comprising:
    a housing having an inlet opening, an outlet opening and an interior conduit defined therein between said inlet opening and said outlet opening; and
    a manipulatable housing valve positioned between said inlet opening and said outlet opening for selectively permitting direct fluid communication between said inlet opening and said outlet opening through said valve;
    said housing valve comprising an elongate member, including a transverse bore, supported within said housing, said elongate member being movable between an open position, in which fluid communication is permitted between said inlet opening and said outlet opening, and a closed position, in which said elongate member occludes fluid communication between said inlet opening and said outlet opening; and
    said bore aligning with said interior conduit when said elongate member is in said open position for permitting fluid communication between said inlet opening and said outlet opening.

2. The device as defined in claim 1, wherein at least one end of said elongate member protrudes through an external surface of said housing, said at least one end of said elongate member being subcutaneously manipulatable for moving said elongate member between said open and closed positions.

3. The device as defined in claim 1, further comprising a biasing device adjacent said elongate member for resiliently urging said elongate member to said closed position.

4. The device as defined in claim 3, wherein said biasing device comprises at least one spring.

5. The device as defined in claim 3, wherein said biasing device comprises a compression chamber.

6. The device as defined in claim 1, further comprising a cannula having a proximal end connected to said housing outlet opening and a distal end connectable to a selected vascular structure.

7. The device as defined in claim 6, wherein said distal end of said cannula includes a manipulatable distal valve positioned adjacent a cannula outlet for selectively permitting fluid communication between said housing outlet opening and said cannula outlet.

8. The device as defined in claim 7, wherein said distal valve is connected to said housing valve whereby manipulation of said housing valve simultaneously activates said distal valve.

9. The device as defined in claim 7, wherein said distal valve comprises a tubular member having an outer wall and an interior passage, said tubular member being movable within said cannula between an open position, in which fluid communication is permitted between said housing outlet opening and said cannula outlet through said interior passage of said tubular member, and a closed position, in which said outer wall of said tubular member occludes said cannula outlet thereby preventing fluid communication between said housing outlet opening and said cannula outlet.

10. The device as defined in claim 9, further comprising a biasing device adjacent said tubular member for resiliently urging said tubular member to said closed position.

11. A method for accessing a vascular structure comprising the steps of: surgically implanting a device having an inlet opening, an outlet opening, an interior conduit defined therein between said inlet opening and said outlet opening and a valve positioned between said inlet opening and said outlet opening;
    said valve comprising an elongate member, including a transverse bore, supported within said device, said elongate member being movable between an open position, in which fluid communication is permitted between, said inlet opening and said outlet opening, and a closed position, in which said elongate member occludes fluid communication between said inlet opening and said outlet opening;
    said bore aligning with said interior conduit when said elongate member is in said open position for permitting fluid communication between said inlet opening and said outlet opening;
    connecting one end of a cannula to said outlet opening and another end of said cannula to a said vascular structure;
    manipulating said valve for permitting direct fluid communication between said inlet opening, said outlet opening, and said vascular structure;
    introducing a needle or needle-introduced catheter through said inlet opening for accessing said vascular structure.

12. The method as defined in claim 11, wherein at least one end of said elongate member protrudes through an external surface of said device, said valve being manipulatable by depressing said at least one end of said elongate member to move said elongate member to said open position.

13. A surgically implantable device for providing intermittent vascular access comprising:
    a housing having a plurality of inlet openings, at least one outlet opening and at least one interior conduit defined therein between said inlet openings and said outlet opening; and
    a manipulatable valve positioned between said inlet openings and said outlet opening for selectively permitting direct fluid communication between said inlet openings and said outlet opening through said valve;
    said valve comprising at least one elongate member, including two or more transverse bores, supported within said housing, said elongate member being movable between an open position, in which fluid communication is permitted between said inlet openings and said at least one outlet opening, and a closed position, in which said elongate member occludes fluid communication between said inlet openings and said outlet opening; and
    said two or more bores aligning with two or more inlet openings when said elongate member is in said open position for permitting fluid communication between said two or more inlet openings and said at least one interior conduit.

14. The device as defined in claim 13, wherein said housing includes two interior conduits isolated from each other and at least one outlet opening in fluid communication with each conduit.

15. The device as defined in claim 13, wherein said housing further includes a button protruding through an external surface of said housing, said button being subcutaneously manipulatable for moving one or more of said elongate members between said open and closed positions.

16. A method for accessing a vascular structure through a plurality of locations on the skin surface comprising the steps of:

surgically implanting a device comprising;
    a housing having a plurality of inlet openings, at least one outlet opening and at least one interior conduit defined therein between said inlet openings and said outlet opening; and
    a manipulatable valve positioned between said inlet openings and said outlet opening for selectively permitting fluid communication between said inlet openings and said outlet opening
    said valve comprising at least one elongate member supported within said housing, said elongate member being movable between an open position, in which fluid communication is permitted between said inlet openings and said at least one outlet opening, and a closed position, in which said elongate member occludes fluid communication between said inlet openings and said outlet opening, said housing including a button protruding through an external surface of said housing, said button being subcutaneously manipulatable for moving one or more of said elongate members between said open and closed positions.

17. The device as defined in claim 16, wherein said housing includes two interior conduits isolated from each other and at least one outlet opening in fluid communication with each conduit.

18. The device as defined in claim 16, wherein said at least one elongate member includes two or more transverse bores formed therethrough, said two or more bores aligning with two or more inlet openings when said elongate member is in said open position for permitting fluid communication between said two or more inlet openings and said at least one interior conduit.

* * * * *